(12) United States Patent
Clark et al.

(10) Patent No.: US 6,689,397 B2
(45) Date of Patent: Feb. 10, 2004

(54) IDENTIFICATION OF SNAKE REPELLENTS

(75) Inventors: Larry Clark, Fort Collins, CO (US); John A. Shivik, Jr., Fort Collins, CO (US)

(73) Assignee: The United States of America as represented by the United States Department of Agriculture, Washington, DC (US)

( * ) Notice: Subject to any disclaimer, the term of this patent is extended or adjusted under 35 U.S.C. 154(b) by 0 days.

(21) Appl. No.: 10/022,084

(22) Filed: Dec. 17, 2001

(65) Prior Publication Data

US 2002/0131986 A1 Sep. 19, 2002

Related U.S. Application Data

(62) Division of application No. 09/749,481, filed on Dec. 26, 2000, now abandoned.
(60) Provisional application No. 60/173,159, filed on Dec. 27, 1999.

(51) Int. Cl.$^7$ ................................................. A61K 35/78
(52) U.S. Cl. ....................... 424/725; 424/405; 424/736; 424/739; 424/746; 424/747; 424/756; 424/769
(58) Field of Search ................................. 424/405, 725, 424/736, 739, 746, 747, 756, 769

(56) References Cited

U.S. PATENT DOCUMENTS 5,626,834 A * 5/1997 Toriba et al.
5,891,919 A * 4/1999 Blum et al.

FOREIGN PATENT DOCUMENTS

JP 62164602 A * 7/1987
JP 1-294601 * 11/1989

OTHER PUBLICATIONS http://www.healthfoodstore.co.uk/infoaroma.html, 2002.*

* cited by examiner

Primary Examiner—Leon B. Lankford, Jr.
Assistant Examiner—Ruth A. Davis
(74) Attorney, Agent, or Firm—Ancel W. Lewis, Jr.

(57) ABSTRACT

Snake repellents include a repellent composition, an inert carrier and an adjuvant. The snake repellents include an essential oil selected from a group of essentials oils or a reagent from one of the essential oils. Methods of repelling snakes include exposing snakes to the snake repellents by aerosol, vapor or fog.

22 Claims, 5 Drawing Sheets

| Extract | N | Initial Behavior | Initial Latency X | SE | Duration Vigorous Movement X | SE | Duration Slow Movement X | SE |
|---|---|---|---|---|---|---|---|---|
| Anise oil | 11 | VM | 13 | 19 | 122 | 62 | 114 | 53 |
| Cedarwood oil | 10 | VM | 81 | 91 | 207 | 89 | 5 | 15 |
| Cinnamon oil | 15 | VM | 4 | 1 | 150 | 38 | 94 | 26 |
| Citronella oil | 5 | VM | 73 | 57 | 82 | 22 | 181 | 26 |
| Clary sage oil | 10 | VM | 23 | 25 | 124 | 74 | 112 | 59 |
| Ginger oil | 10 | SM | 83 | 83 | 4 | 10 | 195 | 100 |
| Grapefruit oil | 10 | VM | 105 | 137 | 84 | 70 | 125 | 80 |
| Juniper berry oil | 10 | VM | 87 | 117 | 133 | 109 | 110 | 113 |
| Lavender oil | 10 | VM | 76 | 38 | 120 | 87 | 124 | 105 |
| Oleo resin of *Capsicum* | 9 | SM | 296 | 5 | 0 | 0 | 4 | 11 |
| Pennyroyal oil | 8 | VM | 13 | 2 | 37 | 28 | 73 | 38 |
| Rosemary oil | 10 | VM | 65 | 39 | 172 | 126 | 74 | 89 |
| Water | 10 | None | --- | --- | 0 | 0 | 0 | 0 |
| Wintergreen oil | 10 | SM | 48 | 8 | 36 | 10 | 131 | 22 |
| Yucca | 10 | None | --- | --- | 0 | 0 | 0 | 0 |

FIGURE 1

| Behavior | Cluster[a] | | | | |
|---|---|---|---|---|---|
| | I n = 3 | II n = 4 | III n = 4 | IV n = 7 | V n = 3 |
| VM | 43 ± 9 | 52 ± 19 | 3 ± 3 | 82 ± 14 | 0 ± 0 |
| SM | 61 ± 16 | 115 ± 10 | 48 ± 16 | 145 ± 9 | 0 ± 0 |
| LAT | 18 ± 12 | 99 ± 11 | 114 ± 13 | 31 ± 14 | 300 ± 0 |
| TOT | 104 ± 26 | 167 ± 12 | 51 ± 17 | 227 ± 11 | 0 ± 0 |
| % VM | 42 ± 2 | 29 ± 11 | 5 ± 4 | 35 ± 5 | 0 ± 0 |
| % SM | 58 ± 2 | 71 ± 11 | 95 ± 4 | 65 ± 5 | 0 ± 0 |

| Chemical | Code | CAS # | N | % Reacting | Initial Movement | Initial Latency (s) ± SE | Duration VM (s) ± SE | Duration SM (s) ± SE | Total Movement |
|---|---|---|---|---|---|---|---|---|---|
| amyl acetate | AMAC | 628-63-7 | 9 | 100.0* | VM | 3 ±0 | 25 ±3 | 42 ±5 | 69 ±39 |
| m-anisaldehyde | AALD | 591-31-1 | 8 | 87.5* |  | 92 ± |  44 ±11 | 179 ±11 | 223 ±70 |
| trans-anethole | ANTH | 4180-23-8 | 8 | 0.0 |  | 118 ± | 84 ±29 | 145 ±20 | 229 ±58 |
| camphor | CAM |  |  |  |  |  |  | 0 ±0 | 0 ± |
| cineole | CINE | 470-82-6 | 14 | 100.0* | VM | 8 ±2 | 45 ±8 | 90 ±6 | 135 ±25 |
| cinnamaldehyde | CALD | 14371-10-9 | 10 | 100.0* | VM | 7 ±1 | 135 ±6 | 145 ±7 | 280 ±104 |
| cinnamic acid | CACD |  | 5 | 0.0 | NONE |  |  | 0 ±0 | 0 ± |
| citral | CITR | 5392-40-5 | 9 | 100.0* | VM | 9 ±2 | 112 ±22 | 133 ±22 | 244 ±82 |
| ethyl butyrate | EB | 105-54-4 | 10 | 10.0 | SM | 223 ±39 | 9 ±1 | 42 ±1 | 52 ±4 |
| ethylphenyl acetate | EPAC |  | 15 | 75.3* | VM | 87 ±34 | 55 ±11 | 111 ± 6 | 167 ±24 |
| eugenol | EUG | 97-53-0 | 10 | 70.0* | VM | 102 ±43 | 133 ±23 | 42 ± 13 | 175 ±36 |
| geraniol | GERL | 106-24-1 | 10 | 0.0 | NONE |  |  | 104 ±0 | 105 ±9 |
| geranyl acetate | GAC | 105-87-3 | 10 | 100.0* | VM | 17 ±5 | 103 ±29 | 120 ±27 | 223 ±59 |
| d-limonene | LIM | 5989-27-5 | 11 | 27.7 | SM | 259 ±23 |  | 36 ± 0 | 36 ±2 |
| linalool | LIN | 78-70-6 | 11 | 9.1 | SM | 123 ±40 |  | 105 ±0 | 105 ±10 |
| methone | MEN |  | 10 | 100.0* | VM | 10 ±2 | 50 ±6 | 59 ±6 | 109 ±35 |
| methyl anthranilate | MA | 134-20-3 | 9 | 86.9* | VM | 41 ±33 | 35 ±14 | 45 ±4 | 80 ±8 |
| methyl salicylate | MS | 119-36-8 | 10 | 100.0* | VM | 10 ±2 | 39 ±8 | 150 ± 7 | 189 ±60 |
| nerol | NER | 106-25-2 | 10 | 10.0 | SM | 110 ±41 |  | 149 ±0 | 149 ±20 |
| a-pinene | PIN | 7785-26-4 | 9 | 77.8* | VM | 87 ±39 | 73 ±16 | 87 ±5 | 161 ±17 |
| a-terpinene | TER |  | 10 | 10.0 | VM | 111 ±25 | 1111 | 55 ±1 | 59 ±4 |

Figure 4

IDENTIFICATION OF SNAKE REPELLENTS

This application is a division of Ser. No. 09/749,481 filed Dec. 26, 2000 now abandoned and claims the benefit under 35 U.S.C. §119(e) of the U.S. provisional patent application No. 60/173,159 filed Dec. 27, 1999.

TECHNICAL FIELD

The present invention relates to animal repellents and more particularly to snake repellents and methods for repelling snakes from open and enclosed areas.

BACKGROUND ART

The availability of chemical agents for vertebrate pest control varies depending upon the taxon considered. As of 1998 sixty one different active ingredients were registered as mammal control agents with the US Environmental Protection Agency under the Federal Insecticide, Fungicide, and Rodenticide Act (FIFRA) (40 CFR 160) with 41% functioning as lethal control agents and 59% as nonlethal repellents. For bird control about ten ingredients are available agents with 40% being used for lethal control and 60% being used in nonlethal repellents. Prior known mammal and bird repellents are not necessarily effective as snake repellents. Only two products are US EPA registered for snake control. The first product is methyl bromide, and it is used as a lethal fumigant. The second product is advertised as "Dr. T's Snake-A-Way Snake Repellent", and contains naphthalene and sulfur as active agents.

Prior known research efforts to discover and develop effective snake control fall into one of two functional categories: prophylactic or remedial.

Prophylactic products are designed to prevent snakes from accessing areas to be protected, whereas remedial products are designed to extirpate snakes once they have entered an area where they are not desired.

Examples of prophylactic approaches to snake control include physical and chemical barriers. Physical barriers are generally considered to be nonlethal and can include electrical fencing, ordinary fencing, obstructions, polybutene products, or other sticky substances. These methods physically prevent a snake from crossing a protected boundary. Chemical barriers contain chemicals that are used to produce noxious odors or contact irritation. Because of the acute chemical sensibility of snakes such barriers are not crossed because of passive diffusion of the noxious chemical directly around the application zone. Delivery via the passive diffusion methods restricts the zone that the repellent is active.

Remedial methods include lethal and nonlethal methods. Examples of lethal control methods include chemical toxicants. These products are either ingested by the snake, applied to the snake dermally, or applied to the space a snake occupies as a lethal fumigant. Traps and glue boards may be used as lethal or nonlethal remedial methods.

Nonlethal remedial methods include using chemicals repellents, that act as irritants, to motivate a snake to abandon a refugium once it has entered that space. Various organic solvents, such as paint thinners, creosote, kerosene, and flammable oils, have been used for this purpose under experimental situations but these chemicals raise clear safety and environmental concerns. There are no prior known chemicals that are experimentally and practically effective at driving snakes out of refugium that are environmentally safe and safe for humans.

There is a clear need for snake repellents for economic and human health and safety reasons, aside from the aesthetic reason for eliminating a pest species from human habitations. As an example, consider the case for the brown treesnake. Brown treesnakes found their way to the island of Guam as a stowaway in cargo in the late 1940's or early 1950's. Over the years the population has irrupted, achieving densities of 50–100 snakes/ha. Ecologically, this snake population explosion has been devastating to the island's ecology. Nine of eleven endemic island birds, 2 lizards, and 1 bat have been driven to extinction by this effective and abundant predator. The high population densities of snakes has also affected the island's economy, principally by causing power outages when this arboreal snake shorts out electrical power substations. As part of a containment program, the US Department of Agriculture traps and removes snakes around cargo ports to reduce the likelihood that snakes will emigrate to other islands. In addition to the efforts to reduce local populations around high risk shipping and air ports, the USDA inspects cargo using dogs, trained to detect snakes. However, even if a dog were to indicate that a snake may or may not be in pallets of wrapped cargo or cargo containers, there remains a laborious procedure of trying to locate the snake.

Repellents for birds and mammals meeting these safety criteria have been found among natural natural products and human food grade products. Modeling snake repellents after known bird and mammal repellents is unlikely to yield success in identifying snake repellents. Each taxon responds to chemicals as irritants differently. However, species of animals within their respective taxon normally exhibit a uniform response to specific chemical irritants.

Repellency is mediated by chemically sensitive neurons called nociceptors concentrated in the nose, eyes, and mouth. Repellency is the behavioral avoidance of chemicals that promote the sensation of irritation and pain. The important feature for generating the behavioral avoidance to chemical exposure, or repellency, is to expose the nociceptors to the irritating chemicals. Vapor and aerosol repellents that could be applied via portable devices and that would motivate the snake to leave a potentially inaccessible refugium are needed. Natural products and human food grade products with well described human safety information that might also serve as snake repellents would significantly reduce registration costs because significant waivers for toxicity could be obtained.

DISCLOSURE OF THE INVENTION

Snake repellents having a repellent composition, an inert carrier and an adjuvant, and methods to use the snake repellents are disclosed. The repellent composition includes at least one essential oil chosen from the group of anise oil, banana oil, cinnamon oil, clove oil, eucalyptus oil, ginger oil, peppermint oil, oil of wintergreen, sage oil, cedarwood oil, citronella oil, juniper berry oil, and rosemary oil, or at least one reagent derived from these oils chosen from the group of iso-amyl acetate, menthone, methyl anthranilate, eugenol, alpha-pinene, ethyl phenyl acetate, nerol, ethyl butyrate, limonene, linalool, alpha-terpinene, cineol, methyl salicylate, anethole, m-anisaldehyde, citral, geranial acetate, and cinnamaldehyde. Methods to deliver the snake repellents to snakes via aerosol, pressurized vapor, or heated vapor for the purpose of increasing penetration of the snake repellent into the targeted application space and methods to deliver aerosol snake repellents for the purpose of deterring aggressive and attack behavior by snakes so as to enhance human health and safety are disclosed.

BRIEF DESCRIPTION OF THE DRAWINGS

Details of this invention are described in connection with the accompanying drawings in which:

FIG. 1 is a summary tabular view of responses of brown tree snakes to the essential oils of snake repellents embodying feature of the present invention.

FIG. 4 is a summary tabular view of responses of brown tree snakes to the reagents of snake repellents embodying feature of the present invention.

DETAILED DESCRIPTION OF THE INVENTION

Figures 2, 5:
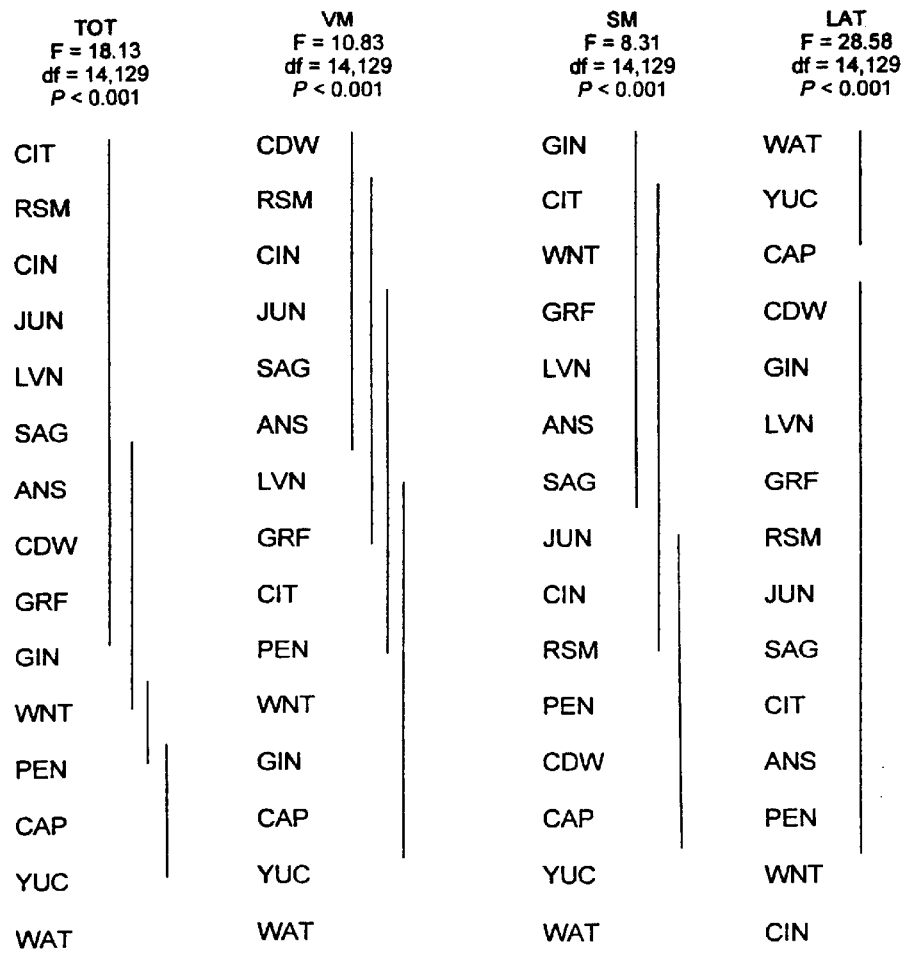
FIG. 2 is a summary graphical view of the data of FIG. 1.
FIG. 5 is a summary tabular view of clusters of the reagents of FIG. 4.

A snake repellent embodying features of the present invention includes a repellent composition, a carrier and an adjuvant. The repellent composition includes at least one essential oil of a plant, or at least one repellent reagent derived from an essential oil. The essential oils are selected from the group of anise oil, cedarwood oil, cinnamon oil, citronella oil, sage oil, ginger oil, grapefruit oil, juniper berry oil, lavender oil, rosemary oil, and oil of wintergreen. The reagents are the principal components of the essential oils and are selected from the group of iso-amyl acetate, m-anisaldehyde, anethole, cineol, cinnamaldehyde, citral, ethyl butyrate, ethyl phenyl acetate, eugenol, geranial acetate, limonene, linalool, menthone, methyl anthranilate, methyl salicylate, nerol, alpha-pinene, and alpha-terpinene. The essential oils from which the reagents are derived are:

| Oil | Reagent |
|---|---|
| anise | trans anethole, m-anisaldehyde |
| basil | linalool (21%), methyl chavicol (73%) |
| birch | methyl salicylate (99%) |
| black pepper | limonene (12%), b-caryophyllene (25%) |
| capsicum | capsaicin |
| cardamon | cineole (29%) |
| cedarwood | caryophyllene |
| cinnamon | cinnamaldehyde, cinnamic acid, benzaldehyde, caryrophyllene, methyl salicylate, |
| citronella | geraniol (24%), geranyl acetate (10%), limonene (7%), |
| clove | eugenol (90%) |
| dill | limonene (23%), carvone (39%), a-phellandrene (22%) |
| eucalyptus | cineol, |
| fennel | anethole (70%) |
| frankincense | a-pinene (26%), limonene (11%) |
| geranium | citronellal, linallool, menthone, phellandrene, pinene |
| lavender | linalool (34%), linalyl acetate (38%) |
| lemon oil | citral, limonene, pinene |
| lemon grass | citral (33%), geranial (45%), geranyl acetate (4%) |
| manderin | limonene (72%), terpinene (17%) |
| marjoram | terpinene (19%), linalool (9%) |
| melaleuca | a-pinene (3%), 1,4-cineol (8%), g-terpinene (20%), linallool (2%), terp.-4-ol (41%) |
| orange | limonene (96%) |
| oregano | linalool (10%), carvacrol (62%) |
| pennyroyal | pulegone |
| peppermint | menthol (32%), menthone (28%), 1,4-cineole (5%) |

-continued

| Oil | Reagent |
|---|---|
| pine | borneol, pinene, terpinene |
| rose | phenethyl acetate |
| rosemary | camphor (10%), 1,4.-cineole (47%) |
| sassafras | camphor, eugenol, linalool, phellandrene, pinene, salicylaldehyde |
| spearmint | limonene, phellandrene, pinene carveol |
| tangerine | limonene (90%) |
| thyme | terpinene, borneol, linalool |
| banana | iso-amyl acetate |
| grapefruit | limonene (95%) |

The carrier is inert, and carries and dilutes the repellent composition. In the preferred embodiment of the snake repellent, the carrier is water. Other carriers may also be used, such as corn oil and propylene glycol. The carrier may also be a propellent such as compressed air. Any inert propellant used in pressurized aerosols also can be used, as for example, dichlorodifluromethane.

The essential oils and repellent reagents are water insoluable. The adjuvant emulsifies and stabilizes the repellent composition in the inert carrier. In the preferred embodiment of the snake repellent, yucca extract is the adjuvant. Yucca extract contains saponins which are a family of detergent chemicals. Other adjuvants may be used, as for example, other detergents such as laural sulfate and Tween 80. By way of example, and not a limitation, the snake repellent could include by weight about 1% repellent composition, 1% adjuvant, and 98% carrier.

The method of the present invention includes the steps of providing a snake repellent including a repellent composition and exposing snakes to the snake repellent. The repellent composition is as described above. More specific methods of exposing snakes to the snake repellent include spraying the snakes with the snake repellent with an aerosol spray, and delivering the snake repellent to the snakes in a vapor, a cold generated fog or a thermal generated fog.

The methods of exposing snakes to the snake repellent differ in the efficiency whereby the chemicals gain access to the nociceptive sensory neurons responsible for the repellent response. Aerosols are liquid particles containing the snake repellent where particle size is generally larger than 10 microns. When these aerosol particles contact the nociceptors of the snakes, the snakes respond by attempting to escape the contaminated atmosphere. Generally aerosols are most effective in direct line of sight delivery because the buoyancy of the particles is limited and the particles do not traverse around corners well.

Vaporized snake repellents consist of gaseous snake repellent where the particle containing the snake repellent is less than 10 microns in diameter. The number of snake repellent molecules per unit volume of air depends on the thermal conditions for which the repellent chemical diffuses into air. Fogs are generated ionically or via pressurized systems. The greater buoyancy of the smaller particles and diffusive capacity of individual molecules provide the vapors and fogs with greater penetration into spaces and around corners than aerosols.

The snake repellents of the present invention were tested as described hereinafter. Brown tree snakes were used to evaluate the efficacy of repellents. While there are taxonomic differences as to what specific chemicals are repellent to specific taxa, there is general uniformity to responsiveness to repellents within a taxon. A given chemical may not be predicted to be repellent to birds or snakes even if it is known to be repellent to mammals. However, chemicals identified to be repellent to one species of bird are highly likely to be repellent to other species of birds. Similar patterns occur for mammals. Hence, it is highly likely that chemicals identified to be repellent to brown tree snakes will be repellent to other snakes as well.

Contrary evidence is given for Dr. T's Snake Away. However, in this circumstance the mode of action of the active ingredients may differ and the mode of deliver does differ. Naphthalene is not an irritant to brown treesnakes. However, sulfur can disrupt cells, releasing endogenous neurochemicals that give rise to pain. High concentrations of sulfur in direct contact with tissue are needed for this to occur. Moreover, Dr. T's products were most effective for snakes that maintain contact with the ground increasing their probability of physical contact with the sulfur. Snakes that had higher tendencies to be arboreal were less repelled by the product, probably because they could avoid contact with a two-dimensional chemical barrier.

Tests of Snake Repellents

Referring to FIGS. 1 to 6, summaries of the testing of the snake repellents embodying features of the present invention are shown.

Study Subjects

Brown tree snakes (*Boiga irregularis*), N=400, were captured on the island of Guam along forest-jungle edge using modified minnow traps with live mice lures or by hand after being spot-lighted on fences. Snakes were individually housed in plastic containers until tested. The holding containers were housed in a military warehouse on Andersen Air Force Base, Guam under a 12:12 light:dark cycle. In general snakes were tested only once. However, some snakes were tested more than once after a latency of at least 5 days, and after it was determined that the snake expressed normal behavior and neurological reactions, i.e., the snake did not show any signs of morbidity, its pupils constricted when lights was shined into them, the snake was aggressive and readily struck at the observer when approached, and it could right itself when turned up side down. Capture of snakes occurred during three separate visits to the island: 1997, 1998, 1999.

Test Compounds

Essential oils and other aroma products (Aromasys) were purchased via retail sales. Essential oils were selected on based on their availability. Reagents used in the tests were selected because they were often the principal compound in the essential oils used, or they were the principal sensory agent of the essential oil. Reagents were purchased from Aldrich Chemical Co., Milwaukee, Wis.

Preparation of Test Formulations

Essential oils and individual chemicals were diluted into an inert carrier liquid (water) for the purpose of testing. An emulsifying agent (3× yucca extract) was added to the composition to stabilize the water insoluble essential oils and individual chemicals in aqueous solution. The test formulations consisted of 1% test agent (i.e., a specific essential oil or chemical), 1% 3× yucca extract and 98% water. The formulated contents were held in a reservoir in which a siphon was suspended. Pressurized air, contained in an aerosol can was passed over the orifice of the siphon to create a negative pressure which would drawn the test formulation up through the siphon and eject the formulated contents and pressurized air through a small bore nozzle to create an atomized liquid, i.e. aerosol spray.

Aerosol Tests

For testing, the holding tub was moved to the observation room and the solid lid was replaced with a lid with a screen insert. Snakes generally did not react overtly to this handling, and remained in a coiled position. Snakes that became active as a result of the handling were not used in the assay. After a 15 min interval where the snake remained in a coiled position, aerosol was sprayed directly onto the snake's head for 2 s at a distance of 30 mm. Immediately after aerosol application, the observer moved to an observation distance of 3 m. We limited observations to the 5 min following aerosol applications. We reasoned that if a compound did not elicit a response within this period, it was unlikely to do so even if longer periods were used. Also, in pilot tests, and with only few exceptions, the escape activity of the snake given an acute (2 s) exposure to the chemical subsided after 5 min.

Behaviors were categorized by a trained observer as follows: VM was a violent, vigorous movement by snakes exposed to the aerosol. This movement was characterized by undirected flailing and vigorous probing of the creases of the test chamber. SM, was characterized as a directed, slow search behavior, often accompanied by tongue flicks. This behavior could also be classified as investigatory behavior. In both cases the duration (s) of these behaviors was noted. The time from the application of the stimulus to the onset of either VM or SM was defined as the latency, LAT-VM and LAT-SM, respectively. For the purposes of analysis we used the latency to the first locomotory behavior, LAT, as the quantifiable metric. TOT was defined as the total amount of time (s) that a snake was engaged in locomatory behavior. The time spent in each locomotory behavior relative to the total active time was defined as % VM and % SM, respectively.

Analyses

We used a fixed effects analysis of variance for the a priori comparison across chemicals. In the first set of analyses, essential oil was the between measures effects while behavior was the dependent variable. We used a post hoc Tukey's Honest Significance Difference test to isolate differences among test stimuli for each of the behavioral measures. Similar analyses were performed for the single reagents. We also categorized reagents into groups that yielded similar combinations of behaviors using cluster analysis (STATISTICA 1999). Amalgamation of clusters was achieved using Ward's method. This approach is distinct from most clustering algorithms in that it uses an analysis of variance approach to evaluate the distances between clusters. The distance measure used was a Chebychev distance. This approach tends to maximize the number of clusters because it is sensitive to differences among objects along single dimensions. The behavioral dimensions considered were: VM, SM, LAT, TOT, % VM, and % SM.

Results

Aerosol Tests for Essential Oils

Figure 3:
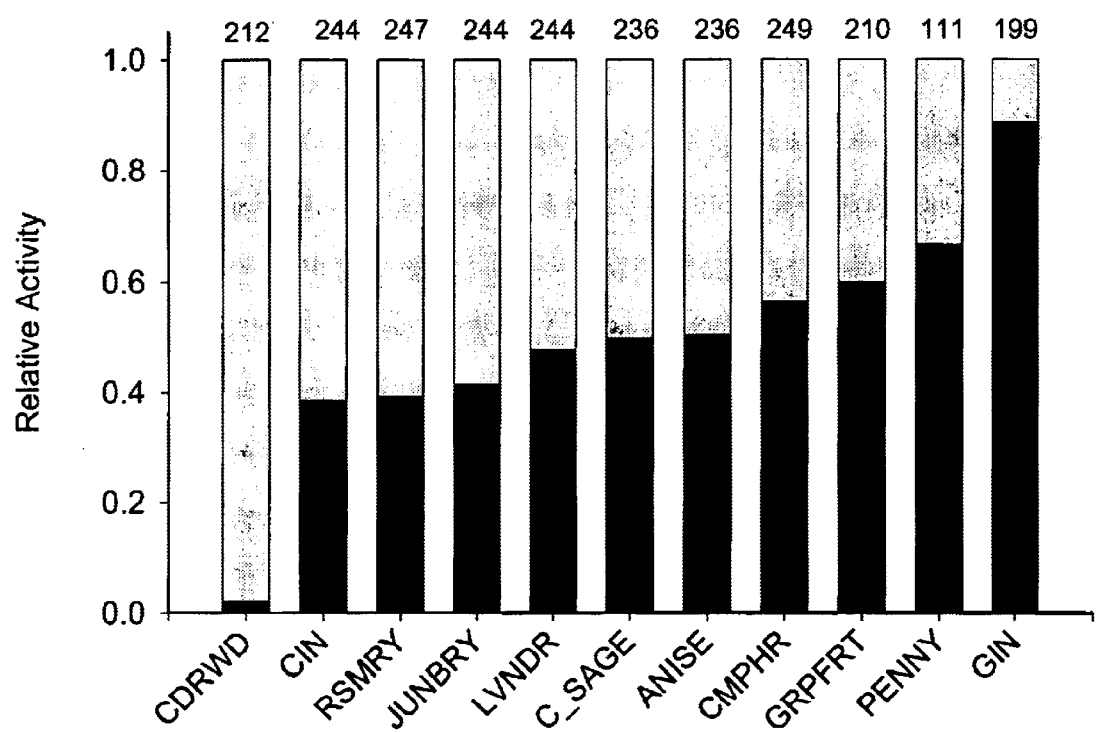
FIG. 3 is a summary graphical view of snake movement times in response to the essential oils of snake repellents embodying feature of the present invention.

FIG. 1 shows a summary of reactions by brown treesnakes to applications of aerosolized essential oils and FIG. 2 shows a comparison of mean behavioral responses by brown treesnakes as a function of essential oil. In FIG. 2 the treatment effect is depicted at the top of each column (one-way fixed effects analysis of variance). Responses to essential oils are ranked from greatest value (top) to least value (bottom). Lines join statistically similar mean responses (P>0.05) as determined by the Tukey's Honestly Significant Difference test with Spjotovoli-Stoline correction for unequal sample sizes (Statistica 2000). Behavioral responses for each analysis included: TOT, total time the snake engaged in locomotory behavior; VM the total time the snakes spent in violent movement; SM the total time the snakes spent in slow investigatory movement, and; LAT the latency for initial movement, irrespective of the type of movement. FIG. 3 shows the proportion of time a snake was observed to be engaged in either slow, directed movement (black) or in undirected vigorous movement (grey). The numbers represent total time (s) a snake was observed to be moving.

Arousal and escape behavior by brown treesnakes resulting from being sprayed by a 2 s application of a natural product-based aerosol varied as a function of treatments. None of the snakes responded to being sprayed with water, thus the precondition for the tests was met. Neither did the snakes behaviorally respond to being sprayed with yucca, the emulsifier used in all tests. Nor were snakes aroused when sprayed with a potent mammalian irritant, oleo resin of Capsicum. Snakes were not aroused when sprayed with the bird and mammalian irritant pennyroyal oil. The remaining essential oils induced arousal in snakes for about the same proportion of the observation period, 56–87%. However, the type of reaction and time observed for each reaction varied as a function of essential oil. The principal response for brown treesnakes sprayed with oil of cedarwood, rosemary, cinnamon, and juniper berry reacted was a prolonged violent, undirected, vigorous. In contrast, the predominant reaction by snakes sprayed with oil of ginger, citronella, wintergreen, and grapefruit was a slow directed investigatory. Snakes sprayed with oil of sage, anise, and lavender reacted with a balance of violent and slow movement. Regardless of the type of reaction snakes showed after being sprayed with essential oil, the latency to first response was similar. Generally snakes grew quiescent before the end of the observation period. However, there was no evidence of chemically induced immobilization as it might affect the snakes' defensive behavior. Snakes either coiled in response to being prodded or they struck at the observer. Two snakes sprayed with cinnamon oil died within 25 hrs of exposure, showing signs of respiratory hemorrhage. All the remaining snakes survived for at least 5 days post treatment with no gross signs of illness or morbidity after which time we stopped monitoring the snakes.

Aerosol Tests for Single Chemicals Frequently Found in Natural Extracts

FIG. 4 shows a summary of reactions by brown treesnakes to applications of aerosolized reagents of the snake repellents of the present invention. Brown treesnakes exhibited the full spectrum of responses to applications of reagent based aerosols. Overall, the response latencies of the snakes' varied considerably across chemicals: latency to initial vigorous movement, F=27.48, df=20,188, P<0.001; latency to initial slow movement, F=9.68, df=20,187, P<0.001. Amyl acetate was characterized by having the shortest latency to response. In post-hoc tests, the compounds that produced movement latencies longer than amyl acetate (P>0.05) were: ethyl butyrate, d-limonene, a-terpinene, linalool, nerol, geraniol, cinnamic acid, and camphor. Snakes exposed to the latter three compounds did not move at all when sprayed with these chemicals. The length of time snakes expressed vigorous, undirected movement after exposure to aerosol also differed across chemicals (F=9.91, df=20,187, P<0.001). Similarly, the length of time snakes expressed slow, directed movement after exposure to aerosols differed across chemicals (F=5.93, df=20, 187, P<0.001).

Figure 6:
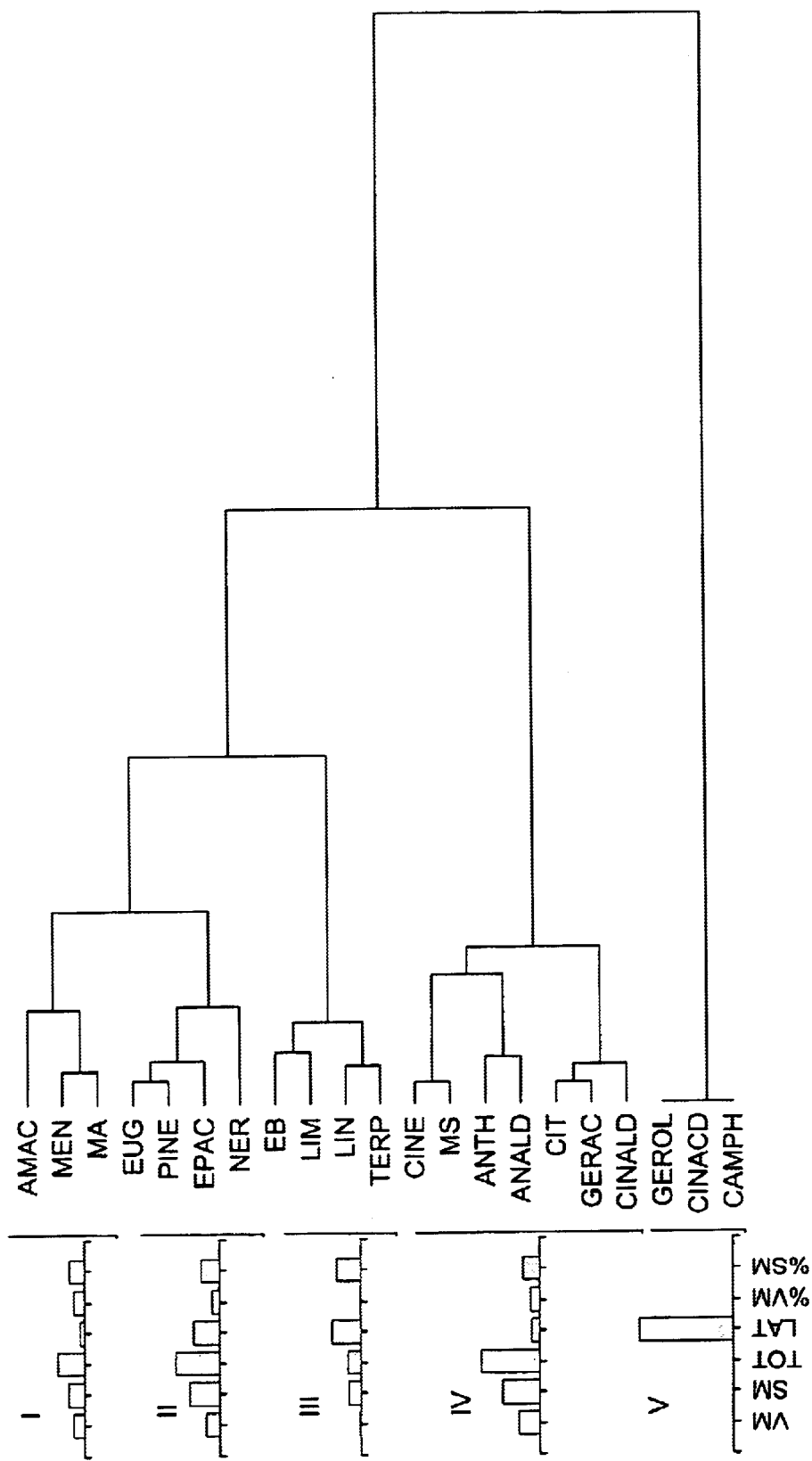
FIG. 6 is a summary graphical view of the clusters of FIG. 5.

To make better sense of the diversity of response values shown in FIG. 4, and to determine whether an underlying pattern of responses to reagents existed we performed a cluster analysis. Referring to FIGS. 5 and 6, five categories of repellents were identified. Cluster values are the mean±SEM behavioral response by brown treesnakes. n is the number of compounds within each cluster. Behaviors used in the cluster analysis were: VM, duration (s) of violent movement; SM, duration (s) of slow, methodical movement; LAT, latency (s) to first movement; TOT, duration (s) of all locomotory behavior; % VM, time spent in violent movement relative to the total movement time; % SM, time spent in slow movement relative to the total movement time.

Brown treesnakes did not react to chemicals in cluster V: geraniol, camphor, and cinnamic acid. Cluster IV can be considered to be the most active chemicals considered, consisting of: trans-anethole, m-anisaldehyde, 1,4-cineole, cinnamaldehyde, citral, geranyal acetate, and methyl salicylate. The snakes' reaction to cluster IV compounds was quick, characterized by a relatively long initial period of violent movement that then gave rise to an extended period of slow investigatory behavior. Cluster II chemicals can be considered moderately active and consisted of: a-pinene, ethyl phenyl acetate, eugenol, and nerol where behavior was characterized by a long period of movement, predominated by slow locomotory behavior. Snakes showed a slight delay in their reactive to being sprayed with Cluster II compounds and were only active for about half of the observation period. As with Cluster IV compounds, the majority of the movement for Cluster II compounds was considered to be slow and methodical. Cluster III compounds can be considered to be only weakly active, and consisted of: ethyl butyrate, limonene, linalool, and □-terpinene. While the initial reaction to cluster III compounds was quick, there was no apparent violent irritation response, and only a short-lived slow investigatory response by snakes. Chemicals in cluster I can also be considered highly irritating, but poor at promoting long-term locomotory behavior. Chemicals is cluster I consisted of: amyl acetate, menthone, and methyl anthranilate.

Although the present invention has been described with a certain degree of particularity, it is understood that the present disclosure has been made by way of example and that changes in details of structure may be made without departing from the spirit thereof.

What is claimed is:

1. A method of repelling snakes comprising the steps of:
providing a snake repellent including a repellent composition selected from the group consisting of cedarwood oil, cinnamon oil, rosemary oil, oil of wintergreen, iso-amyl acetate, m-anisaldehyde, cineol, cinnamaldehyde, ethyl butyrate, ethyl phenyl acetate, eugenol, geranial acetate, menthone, methyl anthranilate, methyl salicylate, and nerol, and
exposing said snakes to said snake repellent.

2. The method of claim 1 wherein said step of exposing includes spraying said snake repellent onto said snakes.

3. The method of claim 1 wherein said step of exposing includes delivering said snake repellent in a vapor to said snakes.

4. The method of claim 1 wherein said step of exposing includes delivering said snake repellent in a cold generated fog to said snakes.

5. The method of claim 1 wherein said step of exposing includes delivering said snake repellent in a thermal generated fog to said snakes.

6. The method of claim 1 wherein said snake repellent includes an inert carrier.

7. The method of claim 6 wherein said carrier is a liquid.

8. The method of claim 7 wherein said liquid is water.

9. The method of claim 6 wherein said carrier is a propellant.

10. The method of claim 1 wherein said snake repellent includes an adjuvant.

11. The method of claim 10 wherein said adjuvant is yucca extract.

12. The method of claim 1 wherein said repellent composition has a concentration in said snake repellent of at least 1% by mass.

13. The method of claim 1 wherein said repellent composition is cinnamon oil.

14. The method of claim 1 wherein said repellent composition is cineol.

15. The method of claim 1 wherein said repellent composition is eugenol.

16. A method of repelling snakes comprising the steps of:
providing a snake repellent including an essential oil of a plant, said plant being selected from the group consisting of cedarwood, cinnamon, clove, eucalyptus, rosemary, peppermint, and wintergreen, and
exposing said snakes to said snake repellent.

17. The method of claim 16 wherein said plant is clove.

18. The method of claim 16 wherein said plant is eucalyptus.

19. A method of repelling snakes comprising the steps of:
providing a snake repellent including a repellent reagent selected from the group consisting of iso-amyl acetate, m-anisaldehyde, cineol, cinnamaldehyde, ethyl butyrate, ethyl phenyl acetate, eugenol, geranial acetate, menthone, methyl anthranilate, methyl salicylate, and nerol, and
exposing said snakes to said snake repellent.

20. The method of claim 19 wherein said reagent is cinnamaldehyde.

21. A method of repelling snakes comprising the steps of:
providing a snake repellent including a repellent composition selected from the group consisting of cinnamon oil, clove oil and eucalyptus oil, and
exposing said snakes to said snake repellent.

22. A method of repelling snakes comprising the steps of:
providing a snake repellent including a repellent reagent selected from the group consisting of cineol, cinnamaldehyde, and eugenol, and
exposing said snakes to said snake repellent.

* * * * *